United States Patent [19]

Ito

[11] 3,994,805

[45] Nov. 30, 1976

[54] ANGLE ROTOR COUNTERCURRENT CHROMATOGRAPHY

[75] Inventor: Yoichiro Ito, Bethesda, Md.

[73] Assignee: The United States of America as represented by the Secretary of the Department of Health, Education and Welfare, Washington, D.C.

[22] Filed: July 22, 1975

[21] Appl. No.: 598,124

[52] U.S. Cl. ............................ 210/31 C; 210/198 C
[51] Int. Cl.² ......................................... B01D 15/08
[58] Field of Search ........... 210/24 C, 198 C; 55/67, 55/197

[56] References Cited
UNITED STATES PATENTS 3,775,309  11/1973  Ito et al. .......................... 210/24 C
3,856,669  12/1974  Ito et al. .......................... 210/24 C

OTHER PUBLICATIONS

"Analytical Biochemistry", vol. 65, pp. 310–320 article entitled Angle Rotor Countercurrent Chromatography, received for publication Sept. 30, 1974.

Primary Examiner—John Adee
Attorney, Agent, or Firm—Browdy and Neimark

[57] ABSTRACT

An apparatus for performing countercurrent chromatography comprises a rotor which holds a coiled helix column at 30° from the vertical. Versatility of the angle rotor is demonstrated on high efficiency separations of biological compounds using a variety of two-phase solvent systems.

6 Claims, 1 Drawing Figure

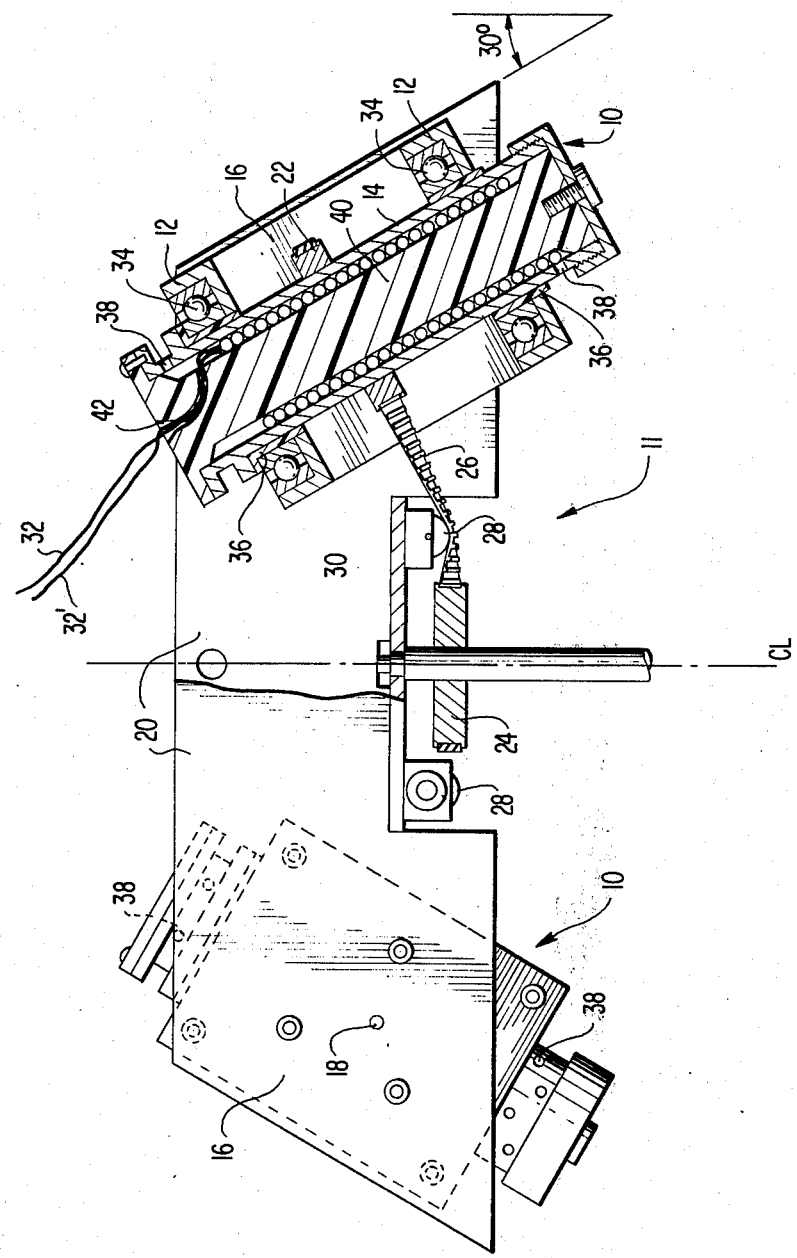

ANGLE ROTOR COUNTERCURRENT CHROMATOGRAPHY

FIELD OF THE INVENTION

The present invention relates to the separation of samples and, more particularly, to a flow-through coil planet centrifuge and a method of countercurrent chromatography employing such a centrifuge. The present invention involves a centrifuge which revolves a helical column, inclined at an angle from the vertical, around the axis of the centrifuge and yet maintains the column in a fixed orientation while it revolves.

BACKGROUND OF THE INVENTION

Separation processes in which two immiscible or partially soluble liquid phases are brought into contact for the transfer of one or more components are referred to as liquid-liquid extraction or solvent extraction. In the simplest case, when two immiscible solvents containing solute are shaken in a separatory funnel and then separated, the solutes are partitioned between the two phases. The ratio of solute concentration in the upper phase to the lower is called the partition coefficient. If the partition coefficient of the two substances differ greatly, the only process needed for separation is a one-step operation. As the nature of the substances become more similar, the difference in their partition coefficients decrease, hence requiring multi-step extraction or separation. When done in countercurrent fashion, this technique is called "the countercurrent distribution method."

Another method of extraction is known as partition chromatography. This method involves a continuous partition process between moving and stationary phases. A variety of methods have been developed for partition chromatography which employ solid supports such as cellulose, silica, alumina, or glass in order to hold one phase stationary. The granular and porous nature of the solid support provides an enormous surface area in relation to the liquid volume and divides the free space into thousands of "plates." In each plate, the partition process is theoretically completed, thus yielding an efficiency as high as thousands of theoretical plates. However, the affinity of the solid supports for the solute can add an undesirable adsorption effect evidenced by tailing of the elution curves of the solutes. When one deals with a minute amount of biological components, adsorption can result in a significant loss or denaturation of samples in addition to contamination by foreign materials eluted from the support.

Another liquid-liquid extraction technique has also been developed which is known as countercurrent chromatography. This system is similar to the countercurrent distribution method in that the two immiscible phases pass through each other in a tubular space. However, it involves a continuous non-equilibrium partition process comparable to chromatography. It was developed to achieve a high efficiency chromatographic separation on both a preparative and analytical scale in the absence of solid supports. However, elimination of the solid support creates a number of problems as listed below:

1. How to keep the stationary phase in the column as the moving phase is steadily eluted.
2. How to divide the column space into numerous partition units and reduce laminar flow spreading of the sample bands.
3. How to increase interfacial area.
4. How to mix each phase to reduce mass transfer resistance.

Several arrangements of countercurrent chromatography have been developed. In each system, a tubular column is made to form multiple traps to hold the stationary phase in a segmented pattern while a gravitational or centrifugal force maintains the two-phase states. Relative interface area is increased by decreasing the tubular diameter and/or increasing the number of the phase segments per unit length of the column. In some cases, effective mixing is accomplished by rotational or gyrational motion of the column, while the interface is held stable by gravity or centrifugal force.

Several methods of countercurrent chromatography have been disclosed in the article by Ito and Bowman in "Journal of Chromatographic Science," vol. 8, pages 315–323, June 1970. These methods include helix countercurrent chromatography, droplet countercurrent chromatography and rotation and gyration locular countercurrent chromatography.

In helix countecurrent chromatography, a horizontal helical tube is filled with one phase of a two-phase liquid system. The other phase is introduced at one end of the helix and passes through the first phase according to the vertical direction of flow resulting in alternate segments of the two phases. Continued flow causes displacement of the second phase only with respect to the stationary first phase. A liquid-liquid partition chromatographic system is thus established. Solutes introduced to either phase will undergo separation according to their relative partition coefficients in a manner analogous to that of conventional liquid chromatography but in the absence of a solid support. The force of gravity holds the lower phase stationary while the upper phase is forced therethrough. To enable the countercurrent process to take place inside a very small diameter tube having a maximum of turns, the enhancement of the gravitational field is necessitated. This is achieved by the use of a centrifuge.

In an article by Ito et al. in Analytical Chemistry, vol. 41, pages 1579–1584, October 1969, such a helix countercurrent chromatography method is described using a coil planet centrifuge. This apparatus induces a planetary motion to a helical tube in a manner such that the rotation of the helical tube is extremely slow in comparison with the revolution. In such a system, however, flow becomes difficult because of the need for the rotating seals; therefore, the separation is usually performed within a closed helical tube. Thus, problems of sample introduction and fractionation limit the practical use of the method.

More recently, two improved countercurrent chromatographic shemes have veen devised, both utilizing a coiled tube in a centrifugal field. One is the flow-through coil planet centrifuge with a vertical rotor, disclosed in U.S. Pat. No. 3,755,309, and the other, the elution centrifuge with a horizontal rotor, disclosed in U.S. Pat. No. 3,856,669. Experiments with various two-phase solvent systems have disclosed specific features inherent to each of these schemes. The advantage of the vertical rotor is that a high efficiency partitioning is achieved with a short separation time by providing a vigorous phase mixing. However, it fails to retain the stationary phase of some low interfacial tension phase systems such as polymer phase systems, due to intensive emulsification. On the other hand, the horizontal rotor provides a stable centrifugal force field to retain polymer phase systems but a longer separation time is generally required due to increased mass transfer resistance.

SUMMARY OF THE INVENTION

It is, accordingly, an object of the present invention to overcome the defects of the prior art, such as indicated above.

Another object is to provide for improved separation of one material from another.

Another object of the present invention is to prove an improved method of countercurrent chromatographic separation.

Another object is to provide an improved elution centrifuge capable of various applications including countercurrent chromatography.

In furtherance of these and other objects as will appear in more detail below, a principal feature of the present invention is a countercurrent chromatographic scheme utilizing a rotor which holds a coiled helix column at an angle from the vertical between 10° and 45°. Based on the advantages and disadvantages of the two prior improved countercurrent chromatographic schemes of U.S. Pat. Nos. 3,755,309 and 3,856,699, it was theorized that the different features of these two prior schemes are apparently derived from the difference in rotor angle between the two schemes and, accordingly, there must exist an optimum rotor angle between vertical and horizontal that permits universal application of the solvent systems with a high partition efficiency.

BRIEF DESCRIPTION OF THE DRAWING

The sole FIGURE is a schematic view of an elution centrifuge in accordance with the present invention, taken partly in front elevation and partly in vertical cross section.

For better understanding of the invention, a possible embodiment will now be described with reference to the attached and above briefly described drawing, it being understood that this detailed description is merely exemplary and in no way limitative.

DETAILED DESCRIPTION OF THE DRAWING

In an attempt to provide a system having the best possible features, efforts were made to determine the optimum rotor angle with which capability of the method is demonstrated on separations using a variety of two-phase solvent systems having different physical properties of interfacial tension, viscosity, and density difference between two phases.

In leading up to the preferred embodiment, a rotor was designed, as in the previous schemes of U.S. Pat. Nos. 3,755,309 and 3,856,669, to produce a counter-rotation of the column holder to establish a continuous flow-through system without rotating seals. This device was constructed with a rotor at a fixed angle of 45° as follows: a cylindrical hollow aluminum column holder was supported by a pair of aluminum blocks equipped with bearings, which were then sandwiched by a pair of aluminum side plates to support the column holder at 45° with an accurate bearing alignment. To prevent twisting the flow tubes, counter-rotation of the holder was established by coupling a pair of toothed pulleys of equal diameter, one fixed at the middle portion of the holder and the other on the motor housing at the center of centrifuge drive. A pair of idler pulleys mounted at the bottom plate of the rotor served for changing direction of the running belt at 45°. The rotor was provided with a dummy side made similar to the operative side to facilitate accurate counter-balancing of the rotor. The revolutional speed was continuously regulated from 400 to 1500 rpm at a mean revolutional radius of 20 cm.

Except for constructional details, the above described device operated to provide satisfactory phase retention of the polymer phase systems while improving the rate of separation time compared with the horizontal rotor scheme of U.S. Pat. No. 3,856,669. It was accordingly determined that the best rotor angle for phase retention must be between 0° and 45° from the vertical. Accordingly, a second device was constructed capable of adjusting the rotor angle between angles of 10° and 30° from the vertical by simple adjustment.

The figure shows the design of such an adjustable angle rotor device 10 set at the 30° position on a centrifuge 11. A pair of bearing blocks 12, holding a column holder 14, preferably formed of aluminum, on each side of the rotor 10, is sandwiched between a pair of rectangular plates 16, also preferably of aluminum or the like. Each of the plates 16 is equipped at the middle with a pin 18 that fits into the pin hole made in a side plate 20 which extends across the vertical axis CL of the centrifuge 11 and of the rotor 10. The arrangement allows the column holder blocks 12 to be rotated around the pins 18 without disturbing the bearing alignment and then bolted to the side plate 20 at a selected angle. The basic contruction of the centrifuge 11 is conventional, except for the modifications here described; there may be used, for example, a conventional refrigerated centrifuge such as MSE, Model LR-6.

A toothed pulley 22 is mounted on the column holder 14 and is coupled to a stationary pulley 24 of equal diameter mounted about the axis CL of the centrifuge 11. The coupling of the fixed pulley 24 to the toothed pulley 22 is through a toothed belt 26 and with the aid of a pair of idler pulleys 28 mounted on a bottom plate 30 of the rotor. This coupling establishes counter-rotation of the column holder 14 to prevent twisting of helically coiled flow tubes 32 and 32' through which the fluids pass. The position of the pulley 22 on the column holder 14 and idler pulleys 28 are also adjustable for each angle to provide an adequate tension to the running belt 26.

In the light of test results obtained using the initially constructed 45° angle rotor, several design items were improved. Properly sealed ball bearings 34 (Moffatt Bearing Co., Cat. No. 209-SZZ) were employed, which can hold lubricant much longer and permit easy lubrication with a syringe needle inserted between the inner ring of the bearing and the plastic seal. Between the column holder 14 and the inner race of each bearing a piece of insulating tube 36, e.g. bakelite, was tightly placed to minimize heat conduction and also prevent rotation of the column holder 14 against the bearings 34. In order to cool the column, several side holes 38 were made at the top and bottom of the column holder 14 to allow air flow inside the holder during operation. A cylindrical column support 40, preferably made of delrin plastic, for the helically coiled flow tubes 32 and 32', is tightly secured at the top and bottom of the holder 14 to prevent vibration during operation.

Two types of column configurations may be employed. A straight helix column (not shown) is prepared by winding tubing, preferably of inert plastic such a Teflon, onto the rigid plastic rod to make the column unit. Multiple column units are interconnected in series and tightly mounted in parallel onto the column support. A coiled helix column (shown in the FIG.) is prepared by winding the tubing 32 and 32', e.g. of Teflon, onto a flexible core which in turn is tightly coiled around the column support 40. In order to minimize any adverse effect of Coriolis force, these columns are preferably placed within 1.3 cm from the central axis of the column holder 14 with a mean revolutional radius of 21 cm. Both feed and return tubes 32 and 32' are passed through a center hole 42 of the column support 40 and then held tightly at the center of the upper member of the centrifuge. The flow tubes have been found to serve several months of operation, when protected with a piece of greased silicon rubber tube at each supported end.

Performance of the apparatus has been evaluated at revolutional speeds ranging between 500 and 1300 rpm during a period of 6 months. Mechanical performance of the apparatus was good and the apparatus demonstrated its versitility on high efficiency separations of biological compounds using a variety of two-phase solvent systems as pointed out in more detail below. Determination of the optimum rotor angle was determined as follows:

Example A Series

Both straight and coiled helix columns were prepared from two sizes of Teflon tubing (Zeus Industrial Products, Inc., Raritan N.J.), 0.55 mm and 0.3 mm i.d. for examination.

The polymer phase system composed of 4% polyethylene glycol 6000, 5% dextran T 500, and 0.1 M sodium phosphate (pH 7) was mainly used, but two other phase systems, sec-BuOH/aqueous dichloroacetic acid and n-BuCH/0.01M NaCl containing 1% cetylpyridinium chloride (CPC1), were also chosen for study because of their specific physical properties. Sec-BuOH system has a low interfacial tension but can be retained by a 60° coiled helix column configuration with the vertical rotor. The n-BuOH/aqueous CPCL system shows a high tendency of emulsification and a complete phase separation requires a few hours in a separatory funnel. The polymer phase systems have extremely low interfacial tension, high viscosity, and small density differences between two phases. Because of these properties, the vertical rotor exemplified in U.S. Pat. No. 3,755,309 failed to retain the latter two phase systems even with the 60° flat coiled helix column configuration.

In each example, the column was filled with the stationary phase and the mobile phase was introduced at various flow rates while the rotor was run at a constant speed and at 25° C until the mobile phase was eluted through the column. Percentage of the stationary phase volume retained within the column was calculated from the eluted stationary phase volume and the capacities of the column and the dead space calibrated beforehand.

Phase retention for each phase system was examined at various rotor angles of 10°, 20°, 30°, and 45° at 1200 and 1500 rpm at maximum flow rates of 2.5 ml/hr for 0.55 mm i.d. columns and 1.0 ml/hr for 0.3 mm i.d. columns. At 10°, all phase systems showed poor phase retention of below 30%. At 20°, the sec-BuOH system gave a sufficient phase retention while other two phase systems exhibited intensive carry-over resulting in poad phase retention. At 30° and 45°, however, all phase systems gave sufficient phase retention ranging from 30 to 50% in both column configurations. The straight helix column was found to retain a greater amount of the stationary phase at a given flow rate and revolutional speed, while the coiled helix column yielded a higher partition efficiency demonstrated by partition of bovine insulin and sec-BuOH/aqueous dichloroacetic acid systems.

Example B Series

Capability of the 30° angle rotor was evaluated on separations of biological materials with a variety of two-phase solvent systems of different physical properties. In order to demonstrate analytical potential of the method, a fine coiled helix column, 0.3 mm i.e. and 40 m long with a helix diameter of 1.2 mm, was used throughout unless otherwise specififed. In each separation, the column was filled with the stationary phase and a sample solution was introduced through the feed tube followed by the elution with the mobile phase using a syringe drive (Harvard Apparatus) at the indicated flow rate, while the rotor was run at the indicated revolutional speed. Separations were performed at 25° C unless otherwise indicated. Eluate was monitored through a UV monitor (LKB Uvicord II) at either 276 or 254 nm except for the polymer phase system. In separation of the colony stimulating factor with the polymer phase system, eluted fractions were added to human bone marrow cell culture for colony count, while the total protein contents were estimated by turbidity measurement of 300 nm in 1 M perchloric acid solution.

Example B-1

Chloroform/acetic acid/0.1 N HCl (2:2:1) [Hausmann, W., Weisiger, J. R., and Craig, L. C. (1955) J. Amer. Chem. Soc. 77, 723]: this phase system has a moderately low interfacial tension, low viscosity, and a great density difference between two phases, which is ideal for countercurrent chromatography. At a flow rate of 0.5 ml/hr at 500 rpm, using the upper aqueous phase as a mobile phase, nine DNP amino acids were separated. Sample volume was $10/\mu l$ containing each component in the lower phase at about 1% where solubility permits. All components were eluted out within 17 hours. A similar chromatogram was obtained at a higher flow rate of 1.5 ml/hr at 1000 rpm, and this separation was completed within 6 hours without serious loss of the resolution.

Example B-2

Ethyl acetate/10% acetic acid, 5% NaCl (1:1) [Hurst, R. E., and Ito, Y. (1972) Clinical Chemistry 18, 814]: This phase system has a high interfacial tension and low viscosity and tends to produce a plug flow in the fine bore column in the vertical rotor. However, the present method overcomes the problem of plug flow and five catecholamine metabolities were well separated and eluted out in 13 hours. Applied sample volume was 20 $\mu l$, containing each component at 0.5g% in the lower phase. The lower phase was used as the mobile phase of a flow rate of 1 ml/hr at 1200 rpm.

The same solvent system was applied to detect urinary catecholamine metabolites from patient. Each urine sample was prepared by adding NaCl (5%) and acetic acid (10%) according to the phase composition and 100 $\mu l$ loaded, while the pure sample was dissolved in the lower phase at 0.5 g% for each component and 20 μl charged. Abnormal levels of VMA (4-hydroxy-3-methoxymandelic acid) and HVA (4-hydroxy-3-methoxyphenylacetic acid) were detected from 100 μl of urine. VMA was co-chromatographed with several other compounds but none of the interfered with any of the colorimetric assays for VMA. HVA was completely separated from other compounds.

Example B-3

N-BuOH/aqueous systems: the two-phase systems have moderate interfacial tension and relatively high viscosity, and are extremely useful for partition of various biological compounds. A chromatogram of purines and pyrimidines on a two-phase system composed of n-Bu-OH/ 1M potassium phosphate (ph 6.5) at 1:1 volume ratio [Tinker, J. F., and Brown, G. B. (1948) J. Biol. Chem. 173 585], was obtained at a flow rate of 0.5 ml/hr and at 1200 rpm. The sample was prepared by dissolving each component in the upper phase at 0.1 g% and 10 μl charged. Since partition coefficients of these compounds favor the lower phase, the upper organic phase was used as a mobile phase for better resolution of peaks. Thus, the present method permits a choice of the mobile phase according to partition coefficients of the solutes of interest.

A chromatogram of a set of dipeptides using a gradient elution technique was also obtained. A linear gradient was applied between 1 and 0% dichloroacetic acid on the base of n-BuOH and 0.1 M ammonium formate at 1:1 volume ration [Ito, Y., and Bowman, R. L. (3973) J. Chromatogr. Sci. 11, 284], using the lower phase as a mobile phase. Sample size was 100 μl containing each component at 0.2 g% in the lower phase. All components were separated and eluted out in 6 hours at a flow rate of 1 ml/hr at 1200 rpm. Two pairs of isomers, L-valyl-L-tyrosine and L-tyrosyl-L-valine, L-leucyl-L-tyrosine and L-tyrosyl-L-leucine, were completely separated in this method.

Example B-4

Sec.-BuOH/3% aqueous dichloroacetic acid (1:1) [Ito, Y., Hurst, R. E., Bowman, R. L., and Achter, E. K. (1974) Separation and Purification Methods, 3 (1), 133]: this two-phase system is characterized by low interfacial tension and high viscosity with a high tendency of emulsification. A countercurrent chromatogram of bovime insulin compared with the partition data by countercurrent distribution method on a similar phase system reported by Harfenist and Craig [(1952) J. A. C. S. 74, 3083] was obtained. The CCD revealed a second component, identified as a deaminated form of insulin which was not separable by either electrophoresis or ultracentrifugation. Countercurrent chromatography completely separated the second component from the main peak. Applied sample size was 1 mg dissolved in 50 μl of the lower phase and the separation was performed at a flow rate of 1 ml/hr at 1200 rpm.

Example B-5

Polymer phase system [Albertsson, P. A. (1971) Partition of Cell Particles and Macromolecules, second ed., Wiley-Interscience, New York; and Johansson, G., Hartman, A., and Albertsson, P. A. (1973) Eur. J. Biochem. 33, 379]: In general, polymer phase systems have extremely low interfacial tension, high viscosity and small density difference between the phases and require a considerable time for phase separation. Because of the aqueous/aqueous phase composition, application to the conventional chromatography becomes difficult and therefore the partition relies upon a time consuming countercurrent distribution method. In order to demonstrate applicability of polymer phase systems to the present method, preliminary studies were performed on separation of colony stimulating factor (CSF) [Metcalf, D., and Moor, M. A. S. (1971) in Haemopoietic Cells (Neuberger, A., and Tatum, E. L., eds.), p. 383, North-Holland Publishing Company, Amsterdam] from human embryonic kidney supernatant using a charged poly (ethylene glycol) phase system [Johansson et al, supra] composed of 6% trimethylaminopolyethylene glycol, 6% dextran T 500, and 0.05 M sodium phosphate.

The pH range of the polymer phase system suitable for partition of CSF was determined on test tube experiments and the toxicity of the upper and lower phases was ruled out on bone marrow cell culture. Subsequently, the separation was performed by applying an exponential gradient elution between the starting (pH 4.4) and ending (pH 6.3) media, using the upper phase as a mobile phase. Two milliliter human embryonic kidney supernatant (Flow Laboratories) was lyophilized and dissolved in 2 ml of the upper phase of the starting medium. A coiled helix separation column, 0.55 mm i.d., 18 m long, and 4 ml capacity, was first filled with the lower phase of the starting medium and them 1.2 ml of the above sample solution was introduced at a rate of 0.6 ml/hr at 1300 rpm, followed by gradient elution for 15 hours at 18° C. Thirty fractions, each 0.3 ml, were obtained during run and then 10 fractions were collected from the column. These fractions were added to human bone marrow cell culture for evaluation of CSF activity by colony count, while the total protein was measured by turbidity in 1 M perchloric acid solution at 300 nm with a Beckman spectrophotometer.

CSF was fairly well separated from the rest of the proteins. The CSF activity at the peak was more than twice that of the original sample solution.

Versatility of the 30° angle rotor has been demonstrated on separations using a variety of two-phase systems including a high interfaciel tension ethyl acetate system and a low interfacial tension polymer phase system. These separations are performed with a single column configuration of coiled helix which is easily prepared from a piece of Teflon tubing and the column can be used for many weeks without damage. Once a suitable phase system is found, a proper operating condition is easily found by adjusting a flow rate and revolutional speed, since the method permits a wide range of applicability for phase retention and solute partitioning. Though a fine separation is usually attained with a slow flow rate by an overnight run, a relatively high resolution can be achieved in several hours with a higher flow rate and revolutional speed. Partition efficiency may be further increased by using a smaller bore and/or longer tubing while scaling up can be attained by a large bore column.

It will be obvious to those skilled in the art that various changes may be made without departing from the scope of the invention and the invention is not to be considered limited to what is shown in the drawings and described in the specification.

What is claimed is:
1. In an elution centrifuge comprising:

centrifugation means having a main axis, a separation column mounted on said centrifugation means, said separation column having an axis which is different from the main axis of revolution of said centrifugation means, a feed tube for introducing fluids to said separation column, a return tube for discharging fluids from said separation column, said centrifugation means including means for revolving said separation column about the main axis of revolution of said centrifugation means and for simultaneously rotating said separation column about its axis at the same angular velocity and in an opposite direction to prevent twisting of said feed and return tubes, the improvement wherein
said axis of said separation column is inclined from said main axis of revolution at an angle of 10°–45°.

2. The device of claim 1 wherein said angle of inclination is 30°–45°.

3. A device in accordance with claim 1 comprising means for adjusting said angle of inclination between 10° and 45°.

4. A device in accordance with claim 1 wherein said separation column comprises a helical tube, said feed tube and said return tube being connected to the ends of said helical tube.

5. A device in accordance with claim 1 wherein said centrifugation means comprises a vertical drive shaft at said axis of revolution, a tube holder for supporting said separation column, means for connecting said tube holder to said drive shaft and for maintaining said tube holder at a predetermined distance from said drive shaft and permitting said tube holder to rotate freely on its own axis, a first pulley concentric with said drive shaft and mounted thereabout in fixed position, a second pulley fixedly connected about said tube holder, belt means connecting between said first and second pulleys, and idler pulley means for changing the direction of said belt means.

6. A method of carrying out countercurrent chromatography in an elution centrifuge having a separation column and a feed tube for introducing fluids to the separation column, the method comprising:
filling said separation column through said feed tube with a first solvent, said separation column having an axis of rotation inclined 10° to 45° from the vertical;
centrifuging said filled separation column by revolving said filled separation column about a vertical axis, while simultaneously rotating said separation column about its own inclined axis, the angular velocity of revolution and the angular velocity of rotation being equal and in opposite directions;
introducing a sample solute to be separated into the moving separation column;
pumping a second solvent, immiscible with said first solvent, into the moving separation column; and
recovering the separated solute fractions leaving the separation column.

* * * * *